(12) United States Patent
Dong

(10) Patent No.: US 6,540,773 B2
(45) Date of Patent: Apr. 1, 2003

(54) LOW PROFILE, HIGH STRETCH KNIT PROSTHETIC DEVICE

(75) Inventor: Jerry Q. Dong, Oakland, NJ (US)

(73) Assignee: SciMed Life Systems, Inc., Maple Grove, MN (US)

( * ) Notice: Subject to any disclaimer, the term of this patent is extended or adjusted under 35 U.S.C. 154(b) by 7 days.

(21) Appl. No.: 09/898,097

(22) Filed: Jul. 3, 2001

(65) Prior Publication Data

US 2003/0028239 A1 Feb. 6, 2003

(51) Int. Cl.⁷ .............................. A61F 2/06; D04B 1/22
(52) U.S. Cl. ........................ 623/1.13; 623/1.5; 66/195
(58) Field of Search ................. 623/1.5–1.52, 623/1.13; 66/192–195

(56) References Cited

U.S. PATENT DOCUMENTS

| | | | |
|---|---|---|---|
| 3,255,615 A | 6/1966 | Schwartz | |
| 3,340,134 A | * 9/1967 | Porter et al. | 66/194 |
| 3,474,644 A | * 10/1969 | Frank | 66/195 |
| 4,015,451 A | * 4/1977 | Gajjar | 66/195 |
| 4,043,007 A | 8/1977 | Heimberger | |
| 4,044,575 A | 8/1977 | Krug | |
| 4,193,137 A | * 3/1980 | Heck | 66/194 |
| 4,343,044 A | 8/1982 | Borda et al. | |
| 4,601,940 A | 7/1986 | Fischer | |
| 5,029,457 A | 7/1991 | Gajjar | |
| 5,150,587 A | 9/1992 | Bergmann | |
| 5,163,951 A | 11/1992 | Pinchuk et al. | |
| 5,215,191 A | 6/1993 | Wright | |
| 5,456,711 A | * 10/1995 | Hudson | 623/1.5 |
| 5,569,273 A | 10/1996 | Titone et al. | |
| 5,628,788 A | 5/1997 | Pinchuk | |
| 5,732,572 A | * 3/1998 | Litton | 66/195 |
| 6,120,539 A | 9/2000 | Eldridge et al. | |
| 6,287,316 B1 | * 9/2001 | Agarwal et al. | 606/151 |
| 6,408,656 B1 | * 6/2002 | Ory et al. | 66/195 |

* cited by examiner

Primary Examiner—Corrine McDermott
Assistant Examiner—Suzette J. Jackson
(74) Attorney, Agent, or Firm—Hoffmann & Baron, LLP

(57) ABSTRACT

A radially expandable stent-graft endoprosthesis is provided. The graft included in the stent-graft is a knitted tubular structure circumferentially disposed and securably attached to the stent. The knitted tubular structure has a knit pattern of interlacing yarns in an Atlas or a modified-Atlas pattern to provide greater than 150 percent longitudinal stretchability. A knitted tubular graft and a knitted medical fabric with greater than 150 percent longitudinal stretchability are also provided.

55 Claims, 10 Drawing Sheets

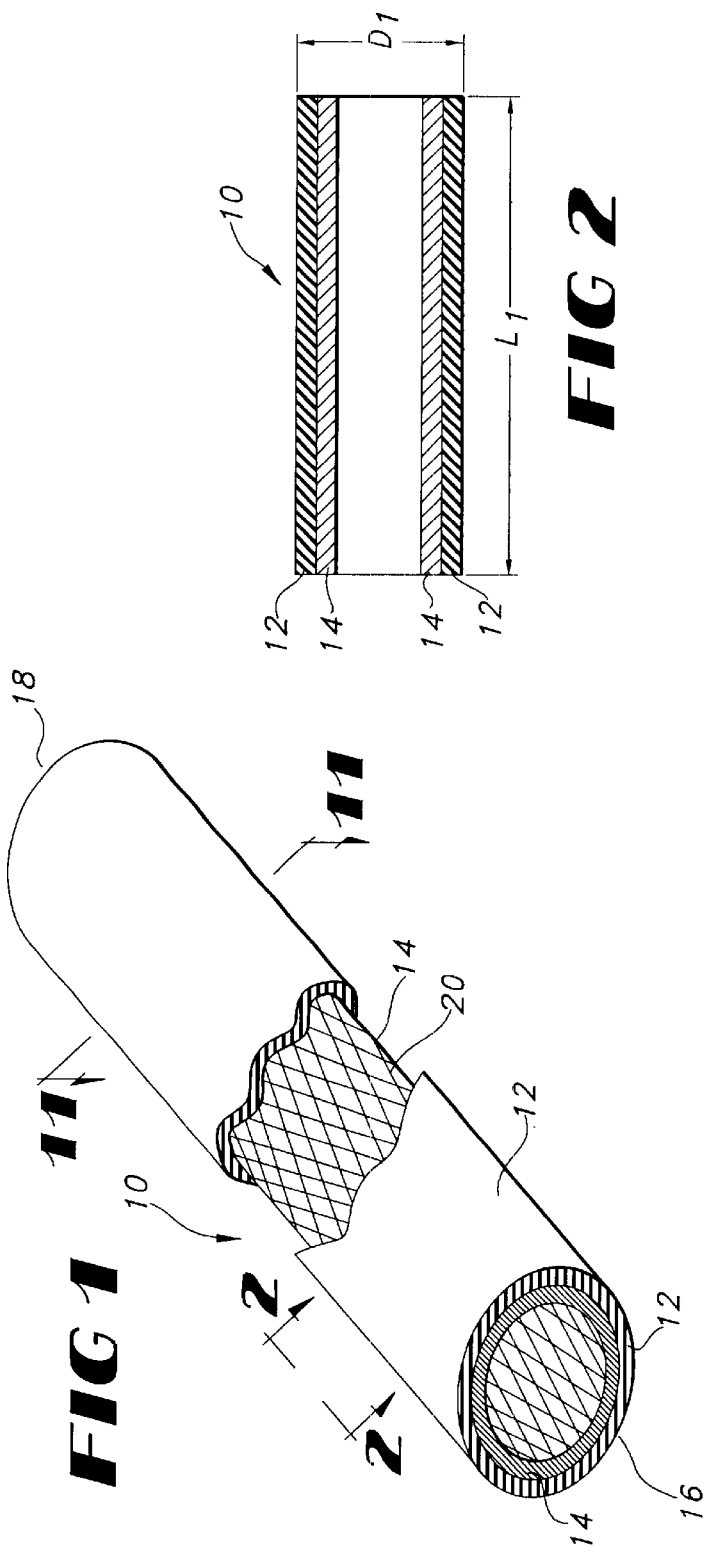

LOW PROFILE, HIGH STRETCH KNIT PROSTHETIC DEVICE

FIELD OF INVENTION

The present invention relates generally to a tubular implantable prosthesis having a knitted textile structure. More particularly, the present invention relates to an endoprosthesis with a knitted textile structure having increased longitudinal stretchability.

BACKGROUND OF RELATED TECHNOLOGY

An intraluminal prosthesis is a medical device used in the treatment of diseased blood vessels. An intraluminal prosthesis is typically used to repair, replace, or otherwise correct a diseased or damaged blood vessel. An artery or vein may be diseased in a variety of different ways. The prosthesis may therefore be used to prevent or treat a wide variety of defects such as stenosis of the vessel, thrombosis, occlusion or an aneurysm.

One type of intraluminal prosthesis used in the repair of diseases in various body vessels is a stent. A stent is a generally longitudinal tubular device formed of biocompatible material which is useful to open and support various lumens in the body. For example, stents may be used in the vascular system, urogenital tract and bile duct, as well as in a variety of other applications in the body. Endovascular stents have become widely used for the treatment of stenosis, strictures and aneurysms in various blood vessels. These devices are implanted within the vessel to open and/or reinforce collapsing or partially occluded sections of the vessel.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Structures which have been used as intraluminal vascular grafts have included coiled stainless steel springs; helically wound coil springs manufactured from a heat-sensitive material; and expanding stainless steel stents formed of stainless steel wire in a zig-zag pattern. Examples of various stent configurations are shown in U.S. Pat. Nos. 4,503,569 to Dotter; 4,733,665 to Palmaz; 4,856,561 to Hillstead; 4,580,568 to Gianturco; 4,732,152 to Wallsten and 4,886,062 to Wiktor, all of whose contents are incorporated herein by reference.

A graft is another commonly known type of intraluminal prosthesis which is used to repair and replace various body vessels. A graft provides a lumen through which blood may flow. Moreover, a graft is often configured to have porosity to permit the ingrowth of cells for stabilization of an implanted graft while also being generally impermeable to blood to inhibit substantial leakage of blood therethrough. Grafts are typically tubular devices which may be formed of a variety of materials, including textile and non-textile materials.

A stent and a graft may combined into a stent-graft endoprosthesis to combine the features thereof. The graft, however, in the stent-graft endoprosthesis should comply with the implantation requirements of the stent which often include collapsing the stent for placement at an implantation site and expansion of the stent for securement thereat. Grafts which cannot easily accommodate the longitudinal and/or radial dimensional changes from a unexpanded or collapsed state to an expanded stent often complicate the implantation of the stent-graft. For instance, some grafts are folded in the collapsed or unexpanded state and must be subsequently be unfolded to accommodate the expanded stent. The unfolding of the graft, however, often complicates the placement of the graft on the stent and the implantation of the stent-graft itself. Alternatively, noncontiguous grafts have been used with expandable stent-grafts. Upon expansion of the stent, however, portions of the noncontiguous graft often separate to accommodate the stent expansion. This separation leaves gaps in the graft structure thereby permitting the leakage of blood through these gaps.

Thus, there is a need for a graft that compliments the implantation of an expandable stent of a stent-graft endoprosthesis. In particular, there is need for a graft that is securably attached to the stent in both the expanded and unexpanded state without complicating the mechanical dynamics of the stent or the graft.

SUMMARY OF THE INVENTION

The present invention provides an implantable tubular prosthesis having a radially expandable tubular stent structure having a first diameter and capable of longitudinal expansion or contraction to achieve a second diameter which is different from the first diameter and a tubular knitted tubular graft circumferentially disposed and securably attached to the stent. The graft has a pattern of interlaced wale and course yarns in a knit pattern to permit longitudinal expansion or contraction of the graft substantially consistent with the longitudinal expansion or contraction of the stent.

The prosthesis of the present invention is capable of longitudinal expansion from 50 to 200 percent by length from a quiescent state. Alternatively, the prosthesis of the present invention is capable of 50 to 200 percent longitudinal contraction by length to achieve a substantially quiescent state from an unexpanded state. Furthermore, the textile graft of the present invention is substantially fluid-tight in its quiescent state.

To achieve such a degree of longitudinal expansion or contraction the textile graft includes a stretchable knit pattern. The pattern is a warp knitted pattern having a set yarns diagonally shifted over one or more yarns to form a loop between engaging yarns. Furthermore, the engaging yarns alternately form open loops where the engaging yarns do not cross over themselves and closed loops where the engaging yarns cross over themselves. The knit pattern is generally described as a Atlas or an modified-Atlas knit pattern. Such patterns depart a high degree of flexibility and stretchability to the textile graft of the present invention.

The knit pattern further includes a plurality of front and back yarns formed from single stitches, where the single stitches are deposed in a plurality of stitch repeating patterns. A first stitch has a repeating pattern traversing diagonally by two or more needle positions and a second stitch has a repeating pattern alternatively traversing diagonally by three or more needle positions and by one needle position.

In one aspect of the present invention an implantable tubular prosthesis capable of longitudinal expansion from a quiescent state to an elongated state in provided. The prosthesis includes a radially contractible and longitudinally expandable tubular stent having a quiescent diameter and quiescent length capable of longitudinal expansion to the elongated state having an elongated length and a contracted diameter, wherein the elongated length is greater than the quiescent length and the contracted diameter is smaller than the quiescent diameter, and further wherein the stent is capable of resiliently returning from the elongated state to the quiescent state. The prosthesis further includes a tubular knitted tubular graft circumferentially disposed and securably attached to the stent in the quiescent state. The graft has a pattern of yarns interlaced into stitches in a knit pattern capable of resilient longitudinal elongation and resilient radial contraction of the graft to the elongated state. Furthermore the graft has from 400 to 900 stitches per square centimeter to provide compliancy in the quiescent state.

In another aspect of the present invention an implantable tubular prosthesis capable of longitudinal expansion from a quiescent state to an elongated state includes a radially contractible and longitudinally expandable tubular stent as described above and a tubular knitted tubular graft having a warp knitted pattern of yarns forming a textile layer having an interior surface and an exterior surface, wherein interior yarns predominate the interior surface and form loops in the longitudinal direction of the prosthesis, and exterior yarns predominate the exterior surface and are diagonally shifted over one or more of the interior yarns in an alternating pattern along a width of the prosthesis to engage the interior yarns. The interior yarn alternately interlaces the engaging exterior yarn to form open loops where the interior yarn does not cross over itself and closed loops where the interior yarn does cross over itself In another aspect of the present invention an implantable tubular prosthesis capable of longitudinal expansion from a quiescent state to an elongated state includes a radially contractible and longitudinally expandable tubular stent and a tubular knitted tubular graft circumferentially disposed and securably attached to the stent in the quiescent state, where the graft has greater than about 350 stitches per square centimeter in its knit pattern to provide compliancy of the graft and wherein the prosthesis is capable of longitudinal expansion from 50 to 200 percent by length.

In yet another aspect of the present invention, an implantable tubular prosthesis capable of longitudinal expansion from a quiescent state to an elongated state includes a radially contractible and longitudinally expandable tubular stent and tubular knitted tubular graft circumferentially disposed and securably attached to the stent. The graft has a knit pattern with greater than about 350 stitches per square centimeter while also having a wall thickness from about 0.3 to about 0.4 millimeters.

In still another aspect of the present invention, an implantable tubular prosthesis capable of longitudinal expansion from a quiescent state to an elongated state includes a radially contractible and longitudinally expandable tubular stent and tubular knitted tubular graft circumferentially disposed and securably attached to the stent, wherein the stent and the graft are resiliently deformable between the quiescent and elongated states and further wherein the graft non-bulgingly contracts from the elongated state to the quiescent state to circumferentially abut the stent.

In still yet another aspect of the present invention, an implantable tubular prosthesis capable of radial expansion from a quiescent state to a radially expanded state includes a radially expandable and longitudinally contractible tubular stent and a tubular knitted tubular graft circumferentially disposed and securably attached to the stent in the quiescent state. The graft has a pattern of yarns interlaced into stitches in a knit pattern capable of resilient radial expansion and resilient longitudinal contraction of the graft to the elongated state and has from 400 to 900 stitches per square centimeter to provide compliancy for the graft in the quiescent state.

In other aspects of the present invention, a non-textile, desirably ePTFE, layer is provided with the endoprosthesis of the present invention. Moreover, a textile graft capable of resilient elongation and having from 400 to 900 stitches per square centimeter is provided. Furthermore, an implantable medical fabric is provided. The medical fabric is a knitted textile with a high degree of stretchability because of the Atlas and the modified-Atlas stitches used to form the fabric. A method for producing the high stretch knit prosthetic device is also provided.

BRIEF DESCRIPTION OF THE DRAWINGS

FIG. 1 is a partial cut-away perspective view of an endoprosthesis of the present invention having a stent and a graft both capable of longitudinal expansion or contraction.

FIG. 2 is a cross-sectional view of the stent-graft of FIG. 1 taken along the 2—2 axis.

FIG. 3 depicts the stent-graft of FIG. 2 having a longitudinally expanded length.

DETAILED DESCRIPTION OF THE INVENTION

Figure 4:
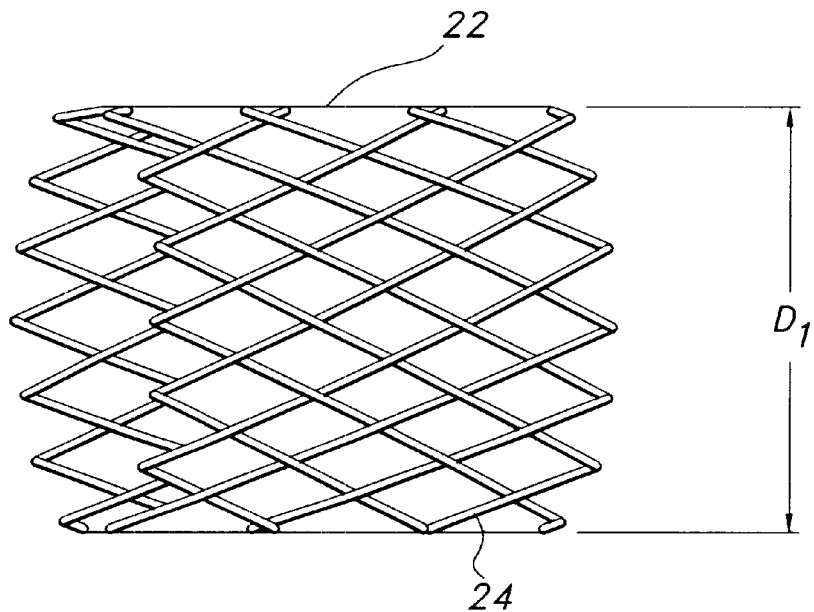
FIG. 4 depicts a wire stent in an expanded state according to the present invention.

The present invention addresses the problems associated with prior art stent-graph endoprosthesis. The stent-graft endoprosthesis of the present invention overcomes the disadvantages of presently available stent-grafts by providing an expandable graft that complements an expandable stent in both an expanded or contracted state. Furthermore, the graft of the present invention is knitted textile graft which provides greater stretchability than previously knitted or woven textile grafts. Moreover, the knitted textile graft of the present invention has a porosity to permit the ingrowth of cells for the stabilization of implanted endoprosthesis while also being generally impermeable to inhibit substantial leakage of blood therethrough.

FIG. 1 is a depiction of stent-graft 10 of the present invention. Stent-graft 10 is shown as a generally tubular structure with open ends 16, 18 to permit the passage of a bodily fluid therethrough. Stent-graft 10 includes textile graft 12 and stent 14. Textile graft 12 extends circumferentially about stent 14. Textile graft 12 is securably attached to stent 14. The attachment of textile graft 12 to stent 14 may be accomplished by mechanically securing or bonding the textile graft 12 and the stent 14 to one and the other. Mechanical securement includes, but is not limited to, the use of sutures, anchoring barbs, textile cuffs and the like. Bonding includes, but is not limited to, chemical bonding, for instance adhesive bonding, thermal bonding and the like.

As depicted in FIG. 1, the textile graft 12 circumferentially extends about an outer stent surface 20. The present invention, however, is not so limited and other stent-graft configurations may suitably be used with the present invention. For instance, textile graft 12 may be circumferentially positioned along an inner surface of stent 14. Moreover, the longitudinal lengths of the stent 14 and the textile graft 12 are not limited to substantially similar lengths as depicted in FIG. 1. For instance, textile graft 12 may be shorter than stent 14 thereby leaving a portion of stent 14 without being covered by textile graft 12.

FIG. 2 dimensionally depicts the stent-graft 10 of the present invention after securement within a bodily lumen (not shown) and FIG. 3 dimensionally depicts the stent-graft 10' prior to securement thereat. To navigate the stent-graft within a bodily lumen the nominal diameter, $D_2$, of stent-graft 10' is smaller than the diameter, $D_1$, of stent-graft 10. Correspondingly, the length, $L_2$, of stent-graft 10' is larger than the length, $L_1$, of stent-graft 10. The textile graft 12 and the stent 14 both conform to these general dimensional depictions for the navigation and securement of stent-graft 10 within a bodily lumen. The textile graft 12 is elongated or stretched to accommodate the elongated stent-graft 10'. Correspondingly, textile graft 12 is in a substantially quiescent state to accommodate the stent-graft 10 of FIG. 2.

Various stent types and stent constructions may be employed in the invention. Useful stents include, without limitation, self-expanding stents and balloon expandable stents. The stents may be capable of radially contracting or expanding, as well, and in this sense can be best described as radially or circumferentially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents.

The configuration of stent 14 may be of any suitable geometry. As shown in FIG. 4, wire stent 22 is a hollow tubular structure formed from wire strand 24 being arranged in what can be described as a "Z" or a "zig-zag" pattern. Wire strand 24 may be formed by, for example, braiding or spinning it over a mandrel. Alternatively, wire stent 24 may be formed from more than one wire strand.

Figure 5:
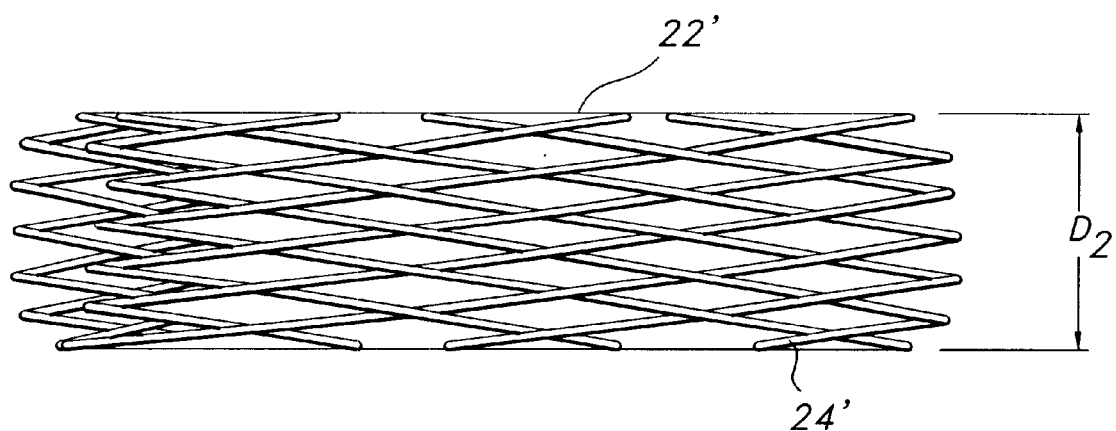
FIG. 5 depicts the wire stent of FIG. 5 in an unexpanded state.

Wire stent 22 is capable of being radially compressed and longitudinally extended, to yield wire stent 22', as depicted in FIG. 5, for implantation into a bodily lumen. The degree of elongation depends upon the structure and materials of the wire stent 22 and can be quite varied. For example, the length of wire stent 22' is from about 50% to about 200% of the length of wire stent 22. The diameter of wire stent 22' may also be up to several times smaller than the diameter of wire stent 22.

Figure 6:
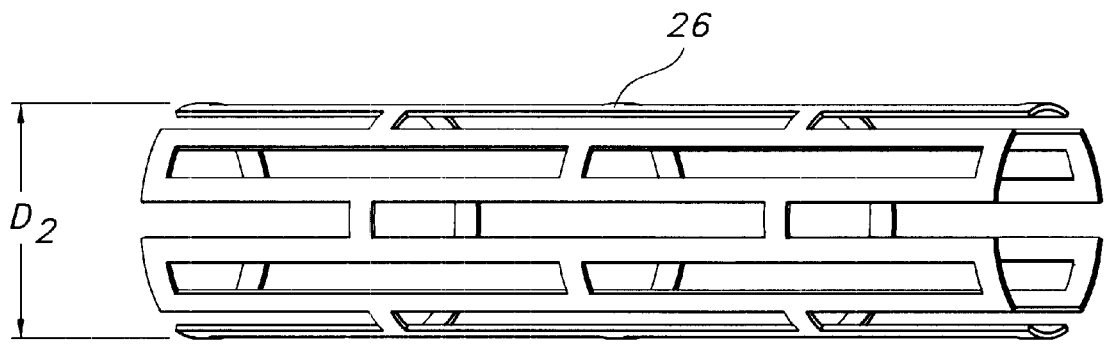
FIG. 6 depicts a slotted stent in a quiescent state according to the present invention.
Figure 7:
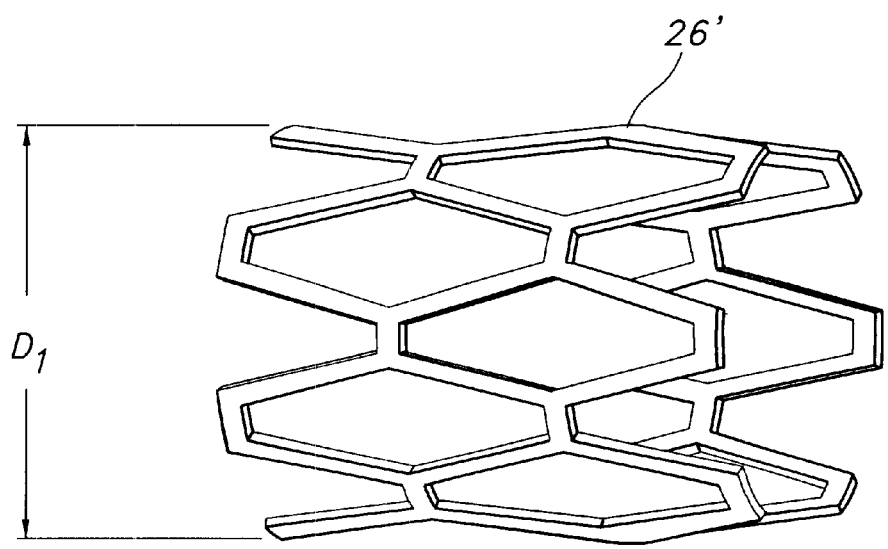
FIG. 7 depicts the slotted-stent of FIG. 6 in an expanded state.

In another aspect of the present invention, a slotted stent 26 is also useful as part of the stent-graft 10. As depicted in FIG. 6, slotted stent 26 is suitably configured for implantation into a bodily lumen (not shown). Upon locating the slotted stent 26 at the desired bodily site, slotted stent 26 is radially expanded and longitudinally contracted for securement at the desired site. The expanded slotted stent 26' is depicted in FIG. 7. Slotted stent 26' is from about 50% to about 200% greater in radial dimension as compared to slotted stent 26.

Figure 8:
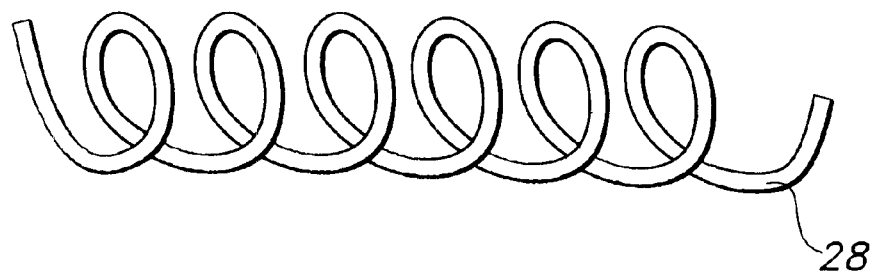
FIG. 8 is a perspective view of a helical coil formed of a single wound wire.
Figure 9:
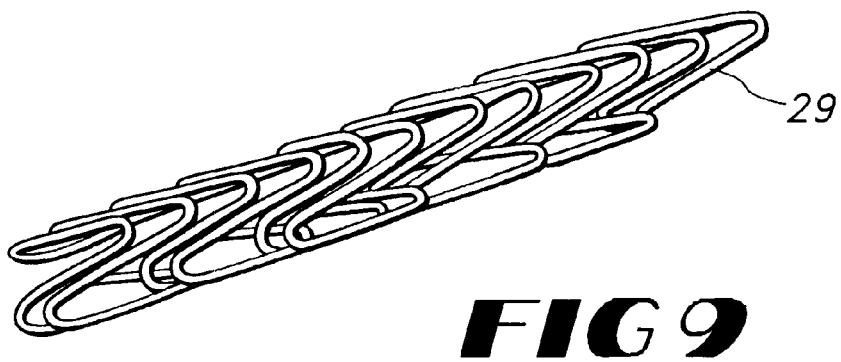
FIG. 9 is a perspective view of a stent having an elongate pre-helically coiled configuration.
Figure 10:
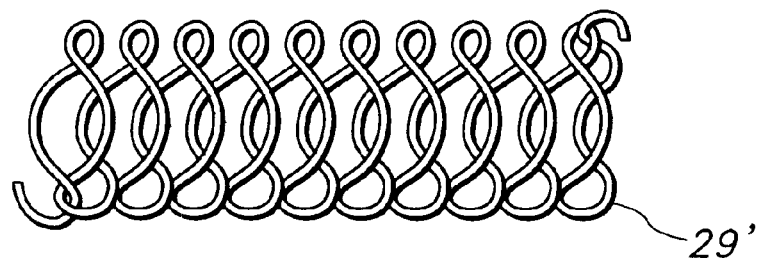
FIG. 10 is a perspective view of the stent of FIG. 9 in a radially expanded state.

Other useful stents capable of radial expansion are depicted in FIGS. 8, 9 and 10. As depicted in FIG. 8, stent 28 is a helical coil which is capable of achieving a radially expanded state (not shown). Stent 29, as depicted FIG. 9, has an elongate pre-helically coiled configuration as shown by the waves of non-overlapping undulating windings. Stent 29 is capable of being radially expanded to expanded stent 29' as depicted in FIG. 10. These helically coiled or pre-helically coiled stents are also useful with the practice of the present invention.

The textile graft 12 is a knitted textile graft. Knitting involves the interlooping or stitching of yarn into vertical columns (wales) and horizontal rows (courses) of loops to form the knitted fabric structure. Warp knitting is particularly useful with the textile graft 12 of the present invention. In warp knitting, the loops are formed along the textile length, i.e., in the wale or warp direction of the textile. For a tubular textile, such as textile graft 12, stitches extending in the axial or longitudinal direction of the tubular textile are called courses and stitches extending along the circumference of the tubular textile are called wales.

Conventional knitted tubular grafts often had to reduce or limit the number of courses per unit length to obtain a flexible tubular structure, i.e., a structure with longitudinal stretchability. Reducing the number of courses per unit length, however, opens the macroporous structure of the textile. A macroporous textile structure is not desirable as a graft because such a structure is not a fluid tight structure, i.e., blood will flow through the graft. Similarly, if the number of wales per unit length was too low, the graft would not seal blood flow. If the number of wales per unit length was too high, the graft could dilate with time. Thus, conventional grafts were limited by the total number of courses and wales per unit length, which is referred to as the number of picks per unit area or the pick size.

For example, textile tubular prostheses in a warp-knit or an Atlas-knit were typically limited to 4 to 16 courses per centimeter (10 to 40 courses per inch) and to 4 to 16 wales per centimeter (10 to 40 wales per inch) to provide a longitudinally stretchable tubular structure. The pick size of these stretchable prostheses were limited to about 16 to 62 stitches per square centimeter (100 to 400 stitches per square inch). The textile graft 12 of the present invention is not so limited because of the novel knit pattern used to form the graft as compared to more conventional knit patterns, such as tricot, locknit and the like, or even previously used Atlas-knits.

Moreover, grafts are sometimes crimped with creases or folds which tend to reduce kinking when the graft is bent. The kinking also allows for some elongation of the graft, but such a crimped graft would not be generally useful as a stent-graft because of the gaps that would result between the stent and the crimped graft.

The textile graft 12 is configured to have a high degree of stretchability. As used herein, the term stretchability and its variants refers to a textile capable of substantially reversible elongation between a quiescent state and a stretched state. Desirably the stretchability of the textile graft 12 is substantially compatible with the dimensional changes associated with an expandable stent having both a expanded and an unexpanded or a contracted state as discussed above. Moreover, textile graft 12 is not a crimped graft and does non-bulgingly contract from the elongated state to the quiescent state. The textile graft 12 substantially abuts the stent along both circumferential and longitudinal portions of the stent without separating or bulging from the stent.

Knitting patterns useful in providing the desired stretchability include those knitting patterns that are not highly interlaced, such as patterns that interlace each adjacent back and front yarn. An example of a highly interlaced and commonly known knitted pattern is a Tricot or Jersey pattern. In contrast the knitting pattern of the present invention is not highly interlaced to provide, among other things, the stretchability of the textile graft for use with an expandable stent.

Figure 11:
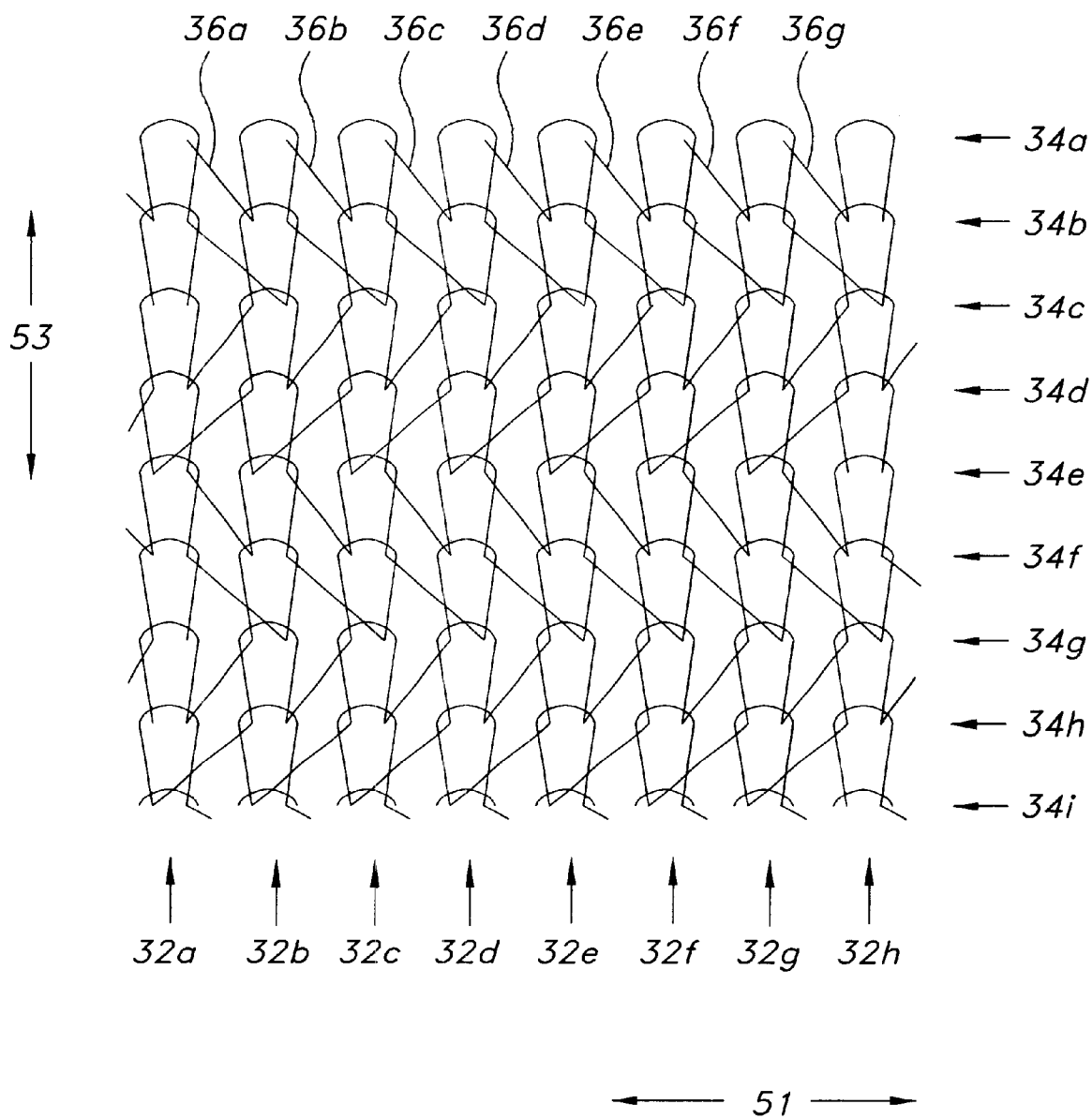
FIG. 11 is a diagrammatic illustration of a textile portion of the graft of FIG. 1 taken along the 11—11 axis.

FIG. 11 is an illustration of a portion 30 of the textile graft 12 taken along the 11—11 axis. The knitted portion 30 is characterized as a warp knit atlas pattern. In FIG. 11, needle position in the course direction, i.e., vector 51, are noted by element numbers 32a through 32h, and needle position s in the wale direction, i.e., vector 53, are noted element numbers 34a through 34i. A yarn moves one needle position in the course direction and one needle position in the wale direction before alternately interlacing with adjacent yarns. The needle positions are indicated by dots 58. For example, yarn 36c moves in the course direction from needle position 32d to needle position 32e, from needle position 32e to needle position 32d, from needle position 32d to needle position 32c, from needle position 32c to needle position 32d, and then repeats this alternating pattern. As yarn 36c moves in the course direction, it also moves generally in wale direction. Adjacent wales and adjacent courses are interlooped to form a warp knitted atlas pattern. The pattern is further described below in conjunction with FIGS. 12 and 13.

The knitted portion 30 is depicted as a single knitted layer in FIG. 11, however, the textile graft 12 of the present invention is not so limited. For instance, the knitted portion 30 may include more than one layer of interconnected yarns. In such a multi-layered knitted textile, yarns from one layer are often interlooped with yarns in another layer to form the multi-layered knitted textile.

Figure 12:
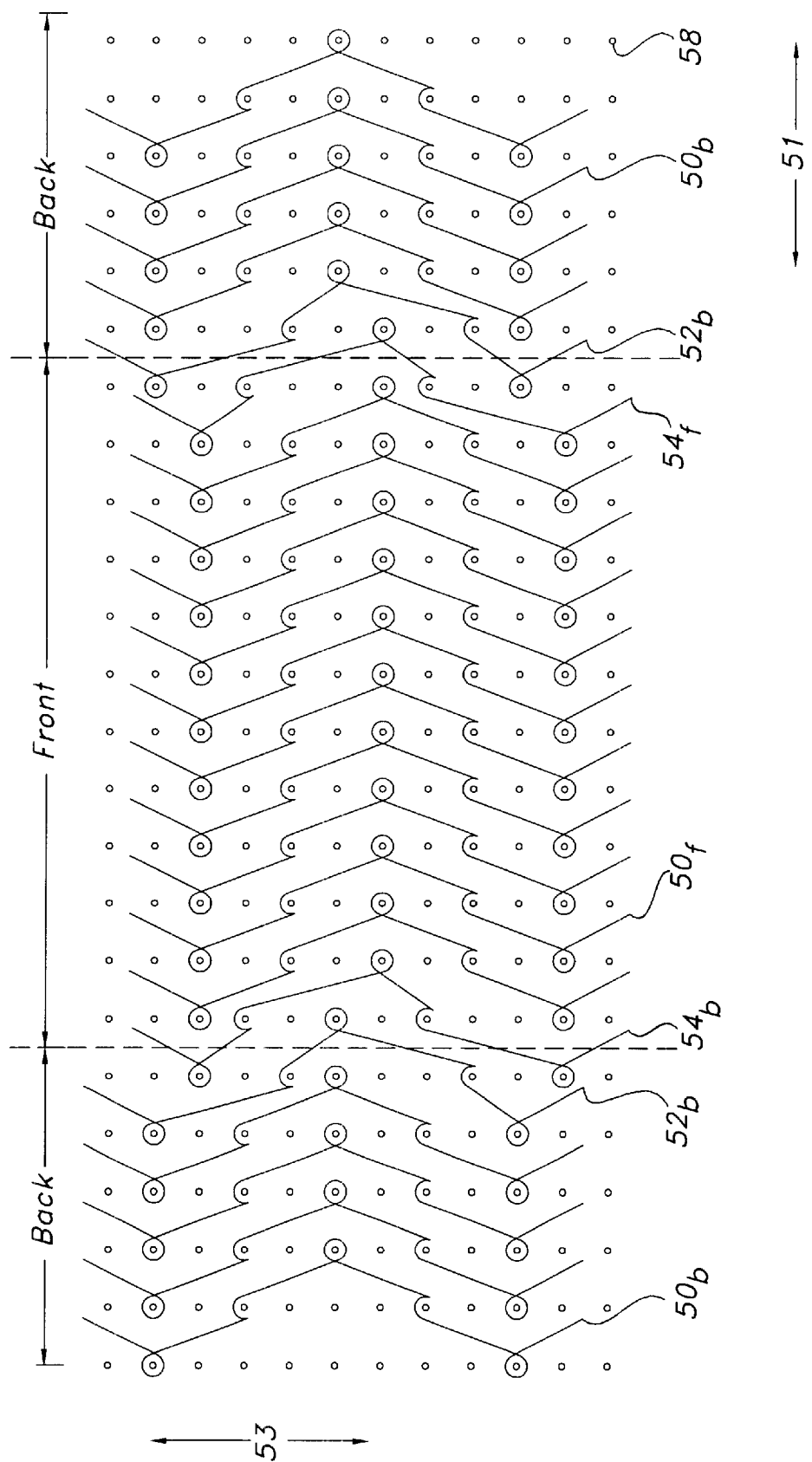
FIGS. 12 and 13 depict yarn patterns for the textile portion of FIG. 11.

Textile graph 12 is flat knitted tubular structure to form such a flat-knitted tubular structure, two portions 30 are co-knitted to one and the other and joined together by border yarns. FIG. 12 depicts the yarn patterns of FIG. 11 by separating front and back yarns from one and the other to more clearly illustrate the individual yarn knit pattern and the repeating nature, if any, of these individual yarn knit patterns. As depicted in FIG. 12, front yarn 50f is repeated about 10 times and then front yarn 54f followed by front yarn 54f are knitted once. This ten-by-one-by-one pattern is repeated to yield a technical front or exterior surface of the textile graft 12. The technical back of the textile graft 10 is depicted in FIG. 12 by repeating back yarn 54b four times followed by repeating back yarns 52b, 54b and 52b and further followed by repeating back yarns 50b four times. This back pattern is repeated to yield the technical back or interior surface of the textile graft 12 of the present invention.

Figure 13:
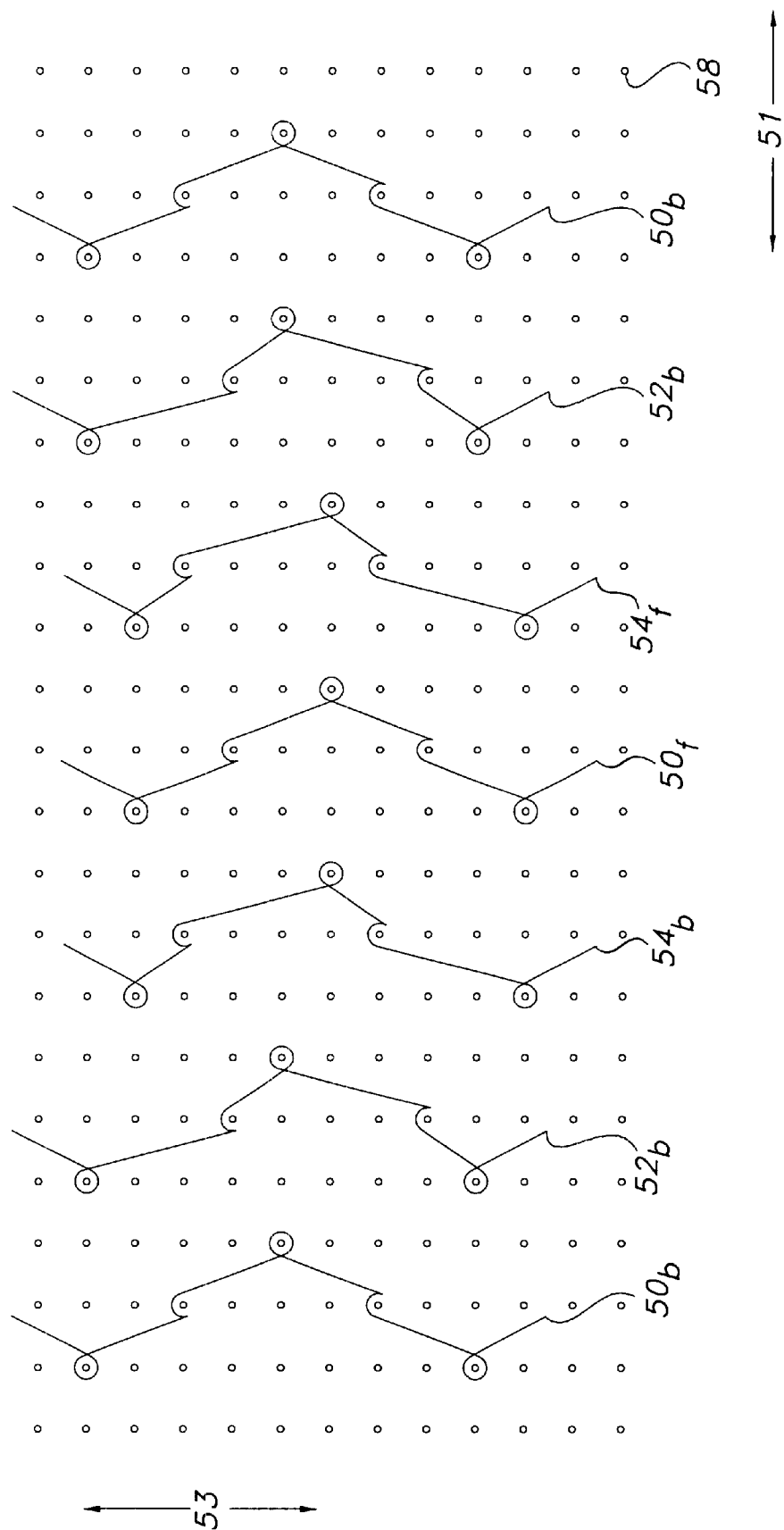

The knitting patterns for the front and back yarns are further illustrated in FIG. 13. The front and back yarns are interlaced in a relatively loose pattern. This pattern may be generally referred to as an Atlas pattern. A warp knit Atlas pattern is generally characterized as a warp knit textile in which a set of yarns shifts diagonally one or more wale per course for several courses, then returns to the original position. In FIG. 13 the course direction is indicated as vector 51 and the warp direction is indicated by vector 53. The knitted pattern of the present invention has multiple patterns of diagonally shifting yarns. Such a pattern provides stretchability to the textile graft 12 and also provides resiliency for the textile graft to substantially return to its quiescent state from its stretched state.

As shown in FIG. 13, front yarns 50f and back yarns 50b shift diagonally by two needle positions in alternating closed-loops and open-loop interlacing structures. The remaining front and back yarns also have alternating and repeating closed-loop and open-loop interlacing structures, but have different needle offsets. For example, back yarn 52b has a closed-loop, an open loop shifted diagonally in a three-by-one needle shift, followed by a closed-loop at a one-by-one needle shift, followed by a three-by-one needle shift for an open-loop and then followed by a closed-loop at an one-by-one needle shift. As used herein, open loops refer to interlacing yarns where a front or a back yarn does not cross over itself in forming the loop. Also, as used herein, closed-loops refer to interlacing yarns where a front or a back yarn crosses over itself in forming the loop. Other patterns useful with the practice of the present invention are illustrated in FIG. 13. All of the different patterns are generally referred to as Atlas or modified-Atlas knit stitches because of their diagonally alternating and repeating patterns.

To knit textile patterns useful with the present invention, double needle bar warp-knitted machine with multiple beams or guide bars is used to form a flat-knitted seamless tubular structure. The threading pattern for each guide bar is shown below in Table 1, and the arrangement of each needle for the guide bar is shown below in Table 2.

TABLE 1

Guide Bar Threading Details

| Guide Bar | y - Threaded/n - Not Threaded Settings | | | | | | | | | | | |
|---|---|---|---|---|---|---|---|---|---|---|---|---|
| 1 | y | y | y | y | y | y | y | y | y | y | n | n |
| 2 | n | n | n | n | n | n | n | n | n | n | y | n |
| 3 | y | n | n | n | n | n | n | n | n | n | n | n |
| 4 | n | n | n | n | n | n | n | n | n | n | n | y |
| 5 | y | n | n | n | n | n | n | n | n | n | n | n |
| 6 | y | y | y | y | y | y | y | y | y | y | n | n |

TABLE 2

Guide Bar Positions

| Guide Bar | Positions |
|---|---|
| 1 | 4-6/4-4/4-2/2-2/2-0/2-2/2-4/4-4/(repeat once) |
| 2 | 2-4/2-2/2-2/0-0/2-0/0-0/0-0/0-2/(repeat once) |
| 3 | 2-2/2-0/2-4/4-4/4-4/4-2/4-2/2-2/(repeat once) |
| 4 | 0-0/0-2/0-2/2-2/2-2/2-2/2-4/2-0/0-0/(repeat once) |

TABLE 2-continued

Guide Bar Positions

| Guide Bar | Positions |
|---|---|
| 5 | 4-2/4-4/4-4/4-2/2-0/2-2/2-2/2-4/(repeat once) |
| 6 | 2-2/2-0/2-2/2-4/4-4/4-6/4-4/4-2/(repeat once) |

The knitted textile graft of the present invention is desirably made on a warp-knitting machine (not shown) using a 14 bar double needle bar Raschel knitting machine. A useful number of needles per centimeter for warp knitting is from about 7 to about 14 (about 18 to about 36 needles per inch). About 11 needles per centimeter (28 needles per inch) are particularly suitable. The textile graft is usually made from a yarn having count from 30 to 300 denier. Desirably, the range of yarn density is from about 30 to about 80 denier. A particularly suitable yarn count is about 40 denier. Moreover, the yarn may be a single ply, a double ply or a multi-ply. The term "multi-ply" is used herein to indicate more than two-ply.

Furthermore, the knitted textile graft of the present invention has greater than 350 stitches per square centimeter, for instance from about 400 to about 900 stitches per square centimeter (about 2,500 to about 6,000 stitches per square inch), to provide compliancy of the graft. Desirably, the present invention has from about 500 to about 700 stitches per square centimeter (about 3,200 to about 4,500 stitches per square inch). Moreover, the knitted textile graft of the present invention has from about 20 to about 30 courses or wales per centimeter (about 50 to about 80 courses or wales per inch) to provide compliancy of the graft. Desirably, the present invention has from about 22 to about 27 courses or wales per centimeter (about 57 to about 67 wales or courses per inch). The number of courses and wales may be the same or different.

In one aspect of the present invention, the knitted textile graft is a knit structure of a single layer with a two-step Atlas movement. Because of the single layer construction the textile wall thickness is minimized to yield a low profile knitted textile graft. The textile wall thickness is from about 0.3 to about 0.4 millimeters. Desirably, the textile wall thickness is from about 0.33 to about 0.36 millimeters. Furthermore, the knitted textile graft of the present invention has a burst strength from about 10 to about 17 kg/cm$^2$ (about 150 psi to about 240 psi). Desirably, the knitted textile graft of the present invention has a burst strength from about 12 to about 14 kg/cm$^2$ (about 170 psi to about 200 psi). The stretchability of the knitted textile graft is 50 to 200 percent at a one-kilogram of load. Knitted textile grafts with a stretchability of about 75 to 180 percent at one-kilogram load are also useful. Furthermore, knitted textile grafts with a stretchability of about 100 to 140 percent at one-kilogram load are also useful.

In a typical method of warp knitting the back yarn is fed from two inside beams, each beam being a spool holding a plurality of ends. Outside beams may be used in conjunction with the inside beams; the outside beams being used for feeding the front yarns. Each outside beam also has a plurality of ends. It should be noted, however, that the inside beams may be used for feeding the front yarn and the outside beams used for feeding the back yarn. Regardless of which beams are used, texturized flat yarn is generally used for both the front and back yarns. The minimum number of beams used in making the textile graft of the present invention is 2. A greater number of beams, however, may be found useful for specific applications. Six guide beams or guide bars have been found to be particularly useful with the practice of the present invention.

Any type of textile product can be used as yarns for the knitted textile graft of the present invention. Of particular usefulness in forming the knitted fabric prosthesis of the present invention are synthetic materials such as synthetic polymers. Synthetic yarns suitable for use in the present invention include, but are not limited to, polyesters, including PET polyesters, polypropylenes, polyethylenes, polyurethanes and polytetrafluoroethylenes. The yarns may be of the monofilament, multifilament, spun type or combinations thereof The yarns may also be flat, twisted or textured, and may have high, low or moderate shrinkage properties or combinations thereof The yarns used in forming the textile grafts of the present invention may be flat, twisted, textured or combinations thereof Furthermore, the yarns may have high, low or moderate shrinkage properties or combination of different shrinkage properties. Additionally, the yarn type and yarn denier can be selected to meet specific properties desired for the prosthesis, such as porosity and flexibility. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used with the present invention may have a denier from about 20 to about 200, preferably from about 30 to about 100. Preferably, the yarns are polyester, such as polyethylene terephthalate (PET), and more preferably the yarns are one ply, 40 denier, 27 filament flat and texturized polyester.

After knitting the textile graft of the present invention is optionally cleaned or scoured in a basic solution of warm water, e.g., about 50° C. to about 65° C. (about 120° F. to about 150° F.), and detergent. The textile is then rinsed to remove any remaining detergent.

After the textile graft is optionally scoured, the graft is compacted or shrunk to reduce and control, in part, the porosity of the graft. Porosity of a knitted material is measured on the Wesolowski scale and by the procedure of Wesolowski. In the Wesolowski test, a fabric test piece is clamped flatwise and subjected to a pressure head of about 120 mm. of mercury. Readings are obtained which express the number of millimeters of water permeating per minute through each square centimeter of fabric. A zero reading represents absolute water impermeability and a value of about 20,000 represent approximate free flow of fluid.

The porosity of the textile graft 12 is often from about 7,000 to about 15,000 on the Wesolowski scale after being knitted on the double needle bar Raschel knitting machine. A more desirable porosity is from about 30 to about 5,000 on the Wesolowski scale and textile graft is compacted or shrunk in the wale direction to obtain the desired porosity. A solution of an organic component, such as hexafluoroisopropanol or trichloroacetic acid, and a halogenated aliphatic hydrocarbon, such as methylene chloride, is used to compact the textile graft by immersing it into the solution for up to 30 minutes at temperatures from about 15° C. to about 160° C. Other compacting solutions may suitably be used, such as those disclosed in U.S. Pat. Nos. 3,853,462 and 3,986,828, whose contents are incorporated by reference herein.

As noted above, preferably the tubular-knitted graft of the present invention is constructed of polyester which is capable of shrinking during a heat-set process. For instance, such grafts are typically flat-knitted in a tubular form. Due to the nature of the flat-knitting process, the tubular graft is generally flat in shape after knitting. Such grafts, however, when constructed of shrinkable polyester yarn, can be heat set on a mandrel to form a generally circular shape.

Such a heat-setting process is accomplished by first knitting the graft in a seamless tubular form out of a material capable of shrinking during a heat-setting or similar process. The graft may be preshrunk before it is placed on a mandrel. Preshrinking may be achieved by submitting the woven graft to moderate temperatures, such as from 90° C. to about 205° C. (about 190° F. to about 400° F.). Usually the graft is placed in a medium for the preshrinking. Such a medium can include without limitation hot water, a chemical fluid, such as methylene chloride, or a gas, such as air or carbon dioxide. The graft of the present invention, however, may suitably be made without such a preshrinking of the yarns.

After the graft is knitted or alternatively knitted and preshrunk, the graft is placed on a mandrel, and heated in an oven at a temperature and time capable of causing the yarns of the graft to heat set to the shape and diameter of the mandrel. Preferably polyester yarns are used, and the heat setting is accomplished at time and temperatures appropriate for the material. For example, heat setting can be accomplished at about 90° C. to about 225° C. (about 190° F. to about 437° F.) for a period of about less than an hour. Temperatures in the range of about 130° C. to about 220° C. (about 260° F. to about 428° F.) are also useful. Desirably, temperatures from about 150° C. to about 215° C. (about 300° F. to about 419° F.) are also useful. Desirably, time periods from about 5 to about 30 minutes are useful. More desirably, with time periods from about 10 to about 20 minutes are useful. Other methods of heat setting known in the art may be employed. After such a heat setting process, the graft can be formed into a shape desired for implantation, having a generally circular inner lumen.

Figure 14:
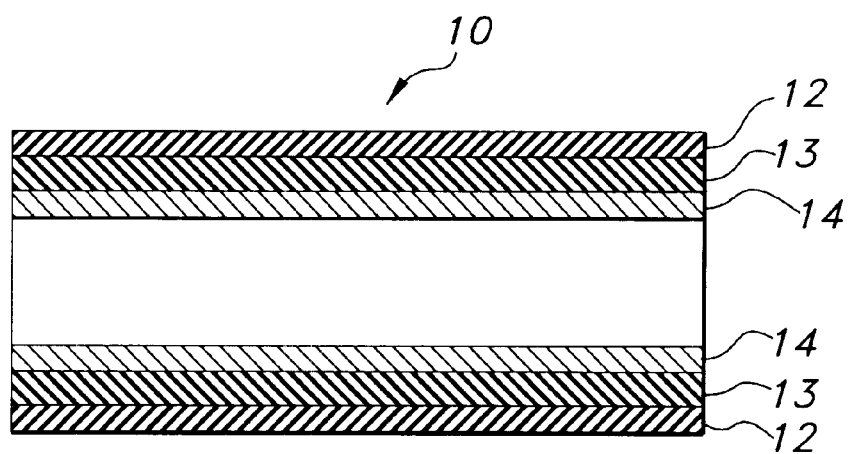
FIG. 14 is a cross-sectional of the present invention which further includes a layer of e-PTFE.

In another aspect of the present invention stent-graft 10 further includes a non-textile layer 13, as depicted in FIG. 14. The non-textile layer is circumferentially disposed between textile graft 12 and stent 14 and securably attached therebetween. One type of non-textile material particularly useful is polytetrafluoroethylene (PTFE). PTFE exhibits superior biocompatibility and low thrombogenicity, which makes it particularly useful as vascular graft material in the repair or replacement of blood vessels. Desirably the non-textile layer is a tubular structure manufactured from expanded polytetrafluoroethylene (ePTFE). The ePTFE material has a fibrous state which is defined by interspaced nodes interconnected by elongated fibrils. The space between the node surfaces that is spanned by the fibrils is defined as the internodal distance. When the term expanded is used to describe PTFE, it is intended to describe PTFE which has been stretched, in accordance with techniques which increase the internodal distance and concomitantly porosity. The stretching may be in uni-axially, bi-axially, or multi-axially. The nodes are spaced apart by the stretched fibrils in the direction of the expansion.

Desirably, the ePTFE material is a physically modified ePTFE tubular structure having enhanced axial elongation and radial expansion properties of up to 600 percent by linear dimension. The physically modified ePTFE tubular structure is able to be elongated or expanded and then returned to its original state without an elastic force existing therewithin. Such a physically modified ePTFE tubular structure is advantageously used in conjunction with wire-stent 22 of stent-graft 10.

Figure 16:
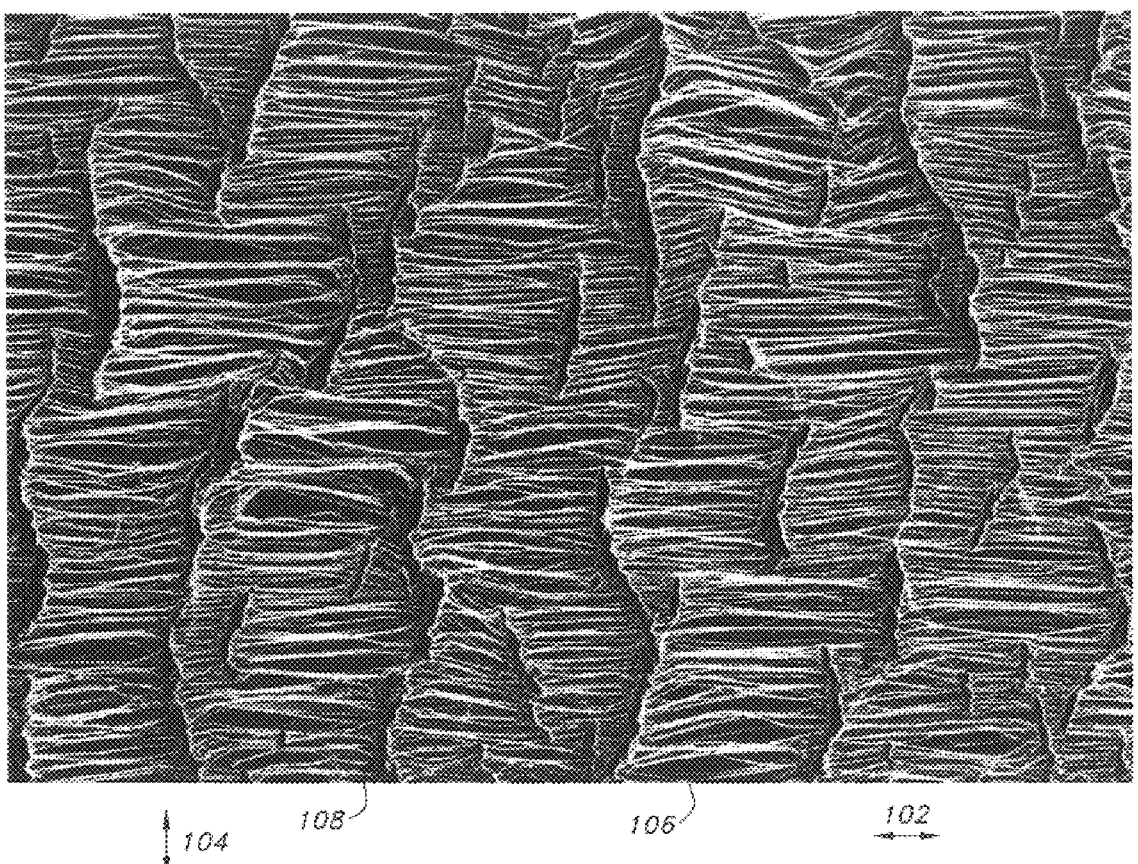
FIG. 16 is a photomicrograph showing a longitudinally expanded ePTFE structure.

FIG. 16 is a photomicrograph of a traditionally longitudinally expanded ePTFE tubular structure. The tube has been stretched in the longitudinal direction shown by directional arrow 102, leaving the nodes circumferentially oriented in circumferential direction shown by the directional arrow 104. The fibrils 106 are shown as being uniformly oriented in the longitudinal direction shown by directional arrow 102. Nodes 108 are shown and are uniformly oriented in circumferential direction 104.

Figure 17:
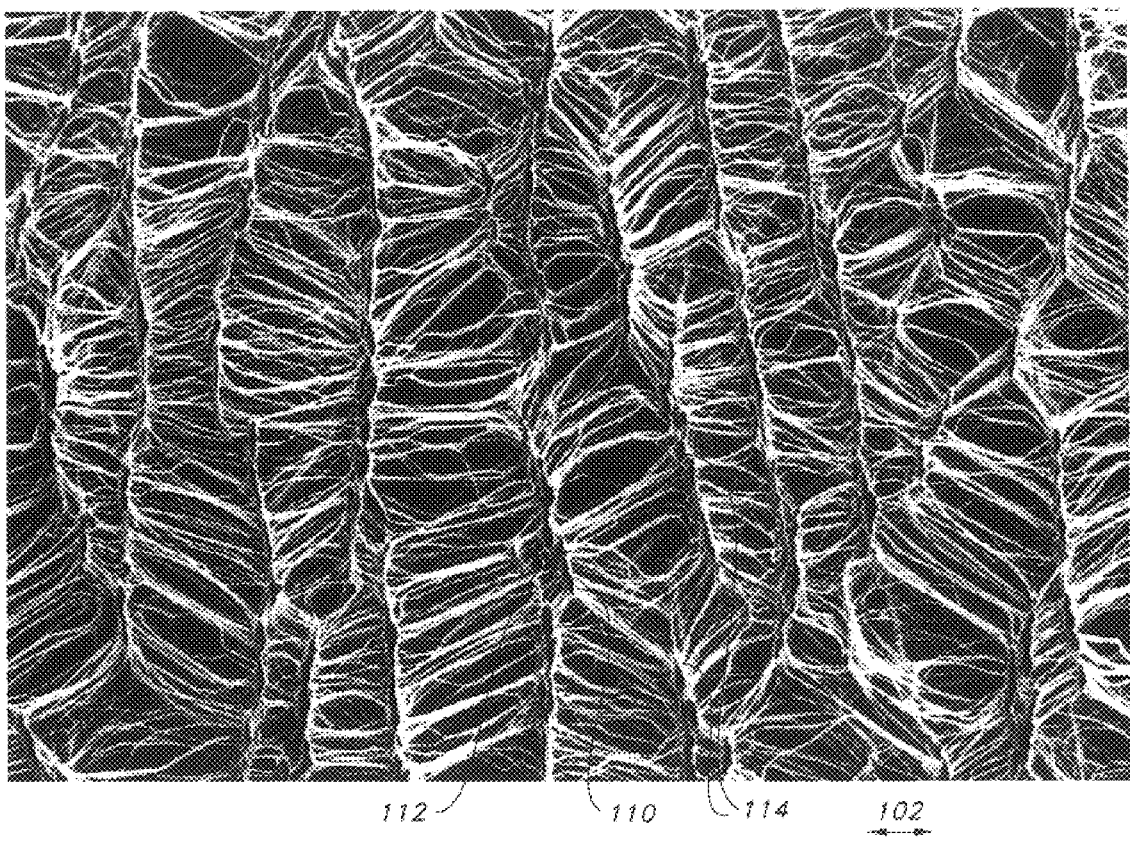
FIG. 17 is a photomicrograph of physically modified ePTFE structure having enhanced elongation properties as compared to the ePTFE structure of FIG. 16.

FIG. 17 is a photomicrograph of the physically modified ePTFE tubular structure having circumferentially oriented nodes and longitudinally traversing fibrils. Nodes 110 are shown in the photomicrograph with a set of fibrils with first ends 112 and second ends 114 attached thereto. The fibrils with first ends 112 and second ends 114 are shown in a hingeably rotated position so that they are not substantially longitudinally oriented in the direction shown by directional arrow 102 as compared to the substantially longitudinally oriented parallel fibril structures 106 of FIG. 16. The term "hingeably rotated" and variants thereof refer to reorientation of previously uniformly oriented line segments by a change in position of one end of each line segment in relation to the other end of each segment, which remains fixed; i.e., the "hinge" about which the other end rotates. The reorientation takes place without a substantial change in dimension of the line segment. Additional details of the physically-modified ePTFE and methods for making the same can be found in commonly assigned application titled, "ePTFE Graft With Axial Elongation Properties", filed on date herewith, attorney docket 498-256, the contents of which are incorporated by reference herein.

Figure 15:
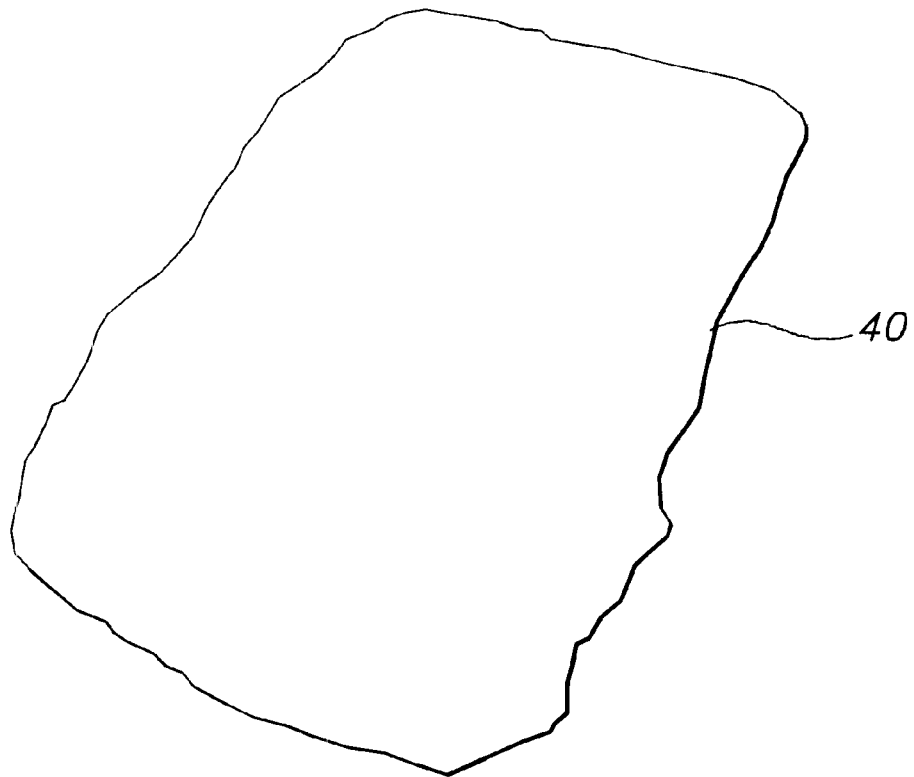
FIG. 15 is a partial perspective view of a knitted medical fabric of the present invention.

FIG. 15 is a partial perspective view of an implantable medical fabric 40, another aspect of the present invention. The medical fabric 40 is a warp-knitted textile fabric having Atlas and modified-Atlas patterns as described above. The medical fabric 40 has the features of the above-described textile graft 12, for instance, a high degree of stretchability. The medical fabric 40 of the present invention is useful in intraluminal applications, such as hernia repair.

The invention may be further understood with reference to the following non-limiting examples.

EXAMPLES

Example 1

Single Layer Knit Tubular Graft With a Two-step Atlas Movement

The following specifications are used to fabricate a solid knitted prosthesis of the present invention.

Yarn Type: Texturized polyethylene terephthalate (PET), 40 denier, 27 filaments.

Number of Guide Bars: Six.

Guide Bar Threading Details: (y—Threaded/n—Not Threaded)

Guide Bar No. 1: y/y/y/y/y/y/y/y/y/y/n
Guide Bar No. 2: n/n/n/n/n/n/n/n/n/y/n
Guide Bar No. 3: y/n/n/n/n/n/n/n/n/n/n
Guide Bar No. 4: n/n/n/n/n/n/n/n/n/n/y
Guide Bar No. 5: y/n/n/n/n/n/n/n/n/n/n
Guide Bar No. 6: y/y/y/y/y/y/y/y/y/n/n
Guide Bar Position Details:
Guide Bar No. 1: 4-6/4-4/4-2/2-2/2-0/2-2/2-4/4-4/(repeat once)
Guide Bar No. 2: 2-4/2-2/2-2/0-0/0-2/0-0/0-0-2/(repeat once)

Guide Bar No. 3: 2-2/2-0/2-4/4-4/4-4/4-2/4-2/2-2/(repeat once)

Guide Bar No. 4: 0-0/0-2/0-2/2-2/2-2/2-4/2-0/0-0/(repeat once)

Guide Bar No. 5: 4-2/4-4/4-4/4-2/2-0/2-2/2-2/2-4/(repeat once)

Guide Bar No. 6: 2-2/2-0/2-2/4-4/4-6/4-4/4-2/(repeat once)

Graft Processing:

Subsequent to knitting the textile graft, the material was scoured in a basic solution of warm water (e.g., about 65° C. or about 150° F.) and cleaning detergent. It was then rinsed to remove the cleaning agents. The graft was then compacted with methylene chloride at elevated temperatures, for instance about 107° C. or about 224° F., for a short period of time, for instance, three minutes.

Next, the prosthesis was heat-set on stainless steel mandrels to achieve the final desired inside diameter. Typically, the outside diameter of the mandrel was twenty to forty percent oversized to impart, in part, a high stretch characteristic to the textile graft. Heat setting was accomplished in a convection oven at about 212° C. (about 414° F.) for about 10 minutes.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An implantable tubular prosthesis capable of longitudinal expansion from a quiescent state to an elongated state comprising:

a radially contractible and longitudinally expandable tubular stent having a quiescent diameter and quiescent length capable of longitudinal expansion to the elongated state having an elongated length and a contracted diameter, wherein the elongated length is greater than the quiescent length and the contracted diameter is smaller than the quiescent diameter, and further wherein said stent is capable of resiliently returning from the elongated state to the quiescent state; and a tubular knitted tubular graft circumferentially disposed and securably attached to said stent in the quiescent state, said graft having a pattern of yarns interlaced into stitches in a knit pattern capable of resilient longitudinal elongation and resilient radial contraction of said graft to the elongated state and having at least about 400 stitches per square centimeter and further having no more than about 900 stitches per square centimeters to provide compliancy in the quiescent state.

2. The prosthesis of claim 1 wherein the elongated length is at least about 50 percent by length greater than the quiescent length; and further wherein the elongated length is no more than about 200 percent by length greater than the quiescent length.

3. The prosthesis of claim 1 wherein said graft has at least about 500 stitches per square centimeter; and further wherein said graph has no more than about 700 stitches per square centimeter.

4. The prosthesis of claim 1 wherein the elongated length is at least about 100 percent by length greater than the quiescent length; and further wherein the elongated length is no more than about 140 percent by length greater than the quiescent length.

5. The prosthesis of claim 1 wherein said graft is substantially fluid-tight in the quiescent state.

6. The prosthesis of claim 1 wherein said knit pattern is a warp knitted pattern of yarns forming a textile layer having an interior surface and an exterior surface, wherein interior yarns comprise the interior surface and form loops in the longitudinal direction of said prosthesis, and exterior yarns comprise the exterior surface and are diagonally shifted over one or more of the interior yarns in an alternating pattern along a width of said prosthesis to engage the interior yarns, and further wherein the interior yarn alternately interlaces the engaging exterior yarn to form open loops where the interior yarn does not cross over itself and closed loops where the interior yarn does cross over itself.

7. The prosthesis of claim 1 wherein said knit pattern is an Atlas or a modified Atlas knit pattern.

8. The prosthesis of claim 1 wherein said knit pattern comprising a interior and exterior yarns interlaced from single stitches, said single stitches being deposed in a plurality of stitch repeating patterns, wherein a first stitch has a repeating pattern traversing diagonally by two or more needle positions and a second stitch has a repeating pattern alternatively traversing diagonally by three or more needle positions and then by one needle position.

9. The prosthesis of claim 1 wherein said graft is a single layer of interlaced yarns.

10. The prosthesis of claim 1 wherein said graft has a wall thickness of at least about 0.3 millimeters; and further wherein said graft has a wall thickness no more than about 0.4 millimeters.

11. The prosthesis of claim 1 wherein said graft is securably attached at intermediate positions along the length of said stent.

12. The prosthesis of claim 11 wherein said graft non-bulgingly contracts from the elongated state to the quiescent state to circumferentially abut said stent.

13. The prosthesis of claim 1 wherein said stent has an interior circumferential surface and further wherein said graft is circumferentially disposed to said interior surface.

14. The prosthesis of claim 1 wherein said stent has an exterior circumferential surface and further wherein said graft is circumferentially disposed to said exterior surface.

15. The prosthesis of claim 1 further including a tubular layer of ePTFE circumferentially disposed and securably attached to said stent.

16. The prosthesis of claim 15 wherein said tubular layer of ePTFE is circumferentially disposed between said stent and said graft.

17. The prosthesis of claim 1 wherein said stent is a wire-stent.

18. The prosthesis of claim 1 wherein said yarns are selected from the group consisting of monofilament yarns, multifilament yearns, spun type yarns, flat yarns, twisted yarns, textured yarns, and combinations thereof.

19. The prosthesis of claim 1 wherein said yarns are selected from the group of materials selected from polyesters, polypropylenes, polyethylenes, polyurethanes, polytetrafluoroethylenes or combinations thereof.

20. The prosthesis of claim 19 wherein said polyesters include polyethylene terephthalate polyesters.

21. The prosthesis of claim 1 wherein said yarns are polyethylene terephthalate polyester textured yarns having a denier of at least about 30; and further wherein said polyethylene terephthalate polyester textured yarns have a denier of no more than about 100.

22. The prosthesis of claim 1 wherein said pattern has at least 20 stitches per centimeter in the longitudinal direction of said prosthesis; and further wherein said pattern has no more than about 30 stitches per centimeter in the longitudinal direction of said prosthesis.

23. The prosthesis of claim 1 wherein said pattern has at least about 20 stitches per centimeter along the width of said prosthesis; and further wherein said pattern has no more than about 30 stitches per centimeter along the width of said prosthesis.

24. An implantable tubular prosthesis capable of radial expansion from a quiescent state to a radially expanded state comprising:
   a radially expandable and longitudinally contractible tubular stent having a quiescent diameter and quiescent length capable of radial expansion to the radially expanded state having an expanded diameter and a contracted length, wherein the expanded diameter is greater than the quiescent diameter and the contracted length is smaller than the quiescent length; and
   a tubular knitted tubular graft circumferentially disposed and securably attached to said stent in the quiescent state, said graft having a pattern of yarns interlaced into stitches in a knit pattern capable of resilient radial expansion and resilient longitudinal contraction of said graft to the elongated state and having at least about 400 stitches per square centimeter and further having no more than about 900 stitches per square centimeter to provide compliancy in the quiescent state.

25. The prosthesis of claim 24 wherein the quiescent length is at least about 50 percent by length greater than the contracted length; and further wherein the quiescent length is no more than about 200 percent by greater than the contracted length.

26. The prosthesis of claim 24 wherein said knit pattern is a warp knitted pattern of yarns forming a textile layer having an interior surface and an exterior surface, wherein interior yarns predominate the interior surface and form loops in the longitudinal direction of said prosthesis, and exterior yarns predominate the exterior surface and are diagonally shifted over one or more of the interior yarns in an alternating pattern along a width of said prosthesis to engage the interior yarns, and further wherein the interior yarn alternately interlaces the engaging exterior yarn to form open loops where the interior yarn does not cross over itself and closed loops where the interior yarn does cross over itself.

27. The prosthesis of claim 24 wherein said knit pattern comprising a interior and exterior yarns interlaced from single stitches, said single stitches being deposed in a plurality of stitch repeating patterns, wherein a first stitch has a repeating pattern traversing diagonally by two or more needle positions and a second stitch has a repeating pattern alternatively traversing diagonally by three or more needle positions and then by one needle position.

28. The prosthesis of claim 24 wherein said graft is a single layer of interlaced yarns.

29. The prosthesis of claim 24 wherein said graft has a wall thickness of at least 0.3 millimeters, and further wherein said graft has a wall thickness no more than 0.4 millimeters.

30. The prosthesis of claim 24 further including a tubular layer of e-PTFE circumferentially disposed and securably attached to said stent.

31. The prosthesis of claim 24 wherein said stent is a slotted-stent.

32. The prosthesis of claim 24 wherein said yarns are polyethylene terephthalate polyester textured yarns having a denier of at least about 30; and further wherein said polyethylene terephthalate polyester textured yarns have a denier no more than about 80.

33. The prosthesis of claim 24 wherein said graft is longitudinally stretched to circumferentially encompass said stent in the quiescent state of said prosthesis.

34. An implantable tubular prosthesis capable of longitudinal expansion from a quiescent state to an elongated state comprising:
   a radially contractible and longitudinally expandable tubular stent having a quiescent diameter and quiescent length capable of longitudinal expansion to the elongated state having an elongated length and a contracted diameter, wherein the elongated length is greater than the quiescent length and the contracted diameter is smaller than the quiescent diameter, and further wherein said stent is capable of resiliently returning from the elongated state to the quiescent state; and
   a tubular knitted tubular graft circumferentially disposed and securably attached to said stent in the quiescent state, said graft having a pattern of yarns interlaced into stitches in a knit pattern capable of resilient longitudinal elongation and resilient radial contraction of said graft to the elongated state and having at least about 400 stitches per square centimeter and further having no more than about 900 stitches per square centimeter to provide compliancy in the quiescent state;
   wherein said knit pattern is a warp knitted pattern of yarns forming a textile layer having an interior surface and an exterior surface, wherein interior yarns predominate the interior surface and form loops in the longitudinal direction of said prosthesis, and exterior yarns predominate the exterior surface and are diagonally shifted over one or more of the interior yarns in an alternating pattern along a width of said prosthesis to engage the interior yarns, and further wherein the interior yarn alternately interlaces the engaging exterior yarn to form open loops where the interior yarn does not cross over itself and closed loops where the interior yarn does cross over itself.

35. The prosthesis of claim 34 wherein the elongated length is at least about 50 percent by length greater than the quiescent length; and further wherein the elongated length is no more than about 200 percent by length greater than the quiescent length.

36. The prosthesis of claim 34 wherein said knit pattern comprising a interior and exterior yarns interlaced from single stitches, said single stitches being deposed in a plurality of stitch repeating patterns, wherein a first stitch has a repeating pattern traversing diagonally by two or more needle positions and a second stitch has a repeating pattern alternatively traversing diagonally by three or more needle positions and then by one needle position.

37. The prosthesis of claim 34 wherein said graft has a wall thickness of at least about 0.3 millimeters; and further wherein said graft has a wale thickness of no more than about 0.4 millimeters.

38. The prosthesis of claim 36 further including a tubular layer of e-PTFE circumferentially disposed and securably attached to said stent.

39. The prosthesis of claim 34 wherein said stent is a wire-stent.

40. The prosthesis of claim 34 wherein said yarns are polyethylene terephthalate polyester textured yarns having a denier from about 30 to about 100.

41. An implantable tubular prosthesis capable of longitudinal expansion from a quiescent state to an elongated state comprising:
   a radially contractible and longitudinally expandable tubular stent having a quiescent diameter and quiescent length capable of longitudinal expansion to the elongated state having an elongated length and a contracted diameter, wherein the elongated length is greater than the quiescent length and the contracted diameter is smaller than the quiescent diameter, and further wherein said stent is capable of resiliently returning from the elongated state to the quiescent state; and a tubular knitted tubular graft circumferentially disposed and securably attached to said stent in the quiescent state, said graft having a pattern of yarns interlaced into stitches in a knit pattern capable of resilient longitudinal elongation and resilient radial contraction of said graft to the elongated state and having greater than about 350 stitches per square centimeter to provide compliancy in the quiescent state;

wherein the elongated length is at least 50 percent by length greater than the quiescent length; and further wherein the elongated length is no more than about 200 percent by length greater than the quiescent length.

42. The prosthesis of claim 41 wherein said knit pattern is a warp knitted pattern of yarns forming a textile layer having an interior surface and an exterior surface, wherein interior yarns predominate the interior surface and form loops in the longitudinal direction of said prosthesis, and exterior yarns predominate the exterior surface and are diagonally shifted over one or more of the interior yarns in an alternating pattern along a width of said prosthesis to engage the interior yarns, and further wherein the interior yarn alternately interlaces the engaging exterior yarn to form open loops where the interior yarn does not cross over itself and closed loops where the interior yarn does cross over itself.

43. The prosthesis of claim 41 wherein said knit pattern comprising a interior and exterior yarns interlaced from single stitches, said single stitches being deposed in a plurality of stitch repeating patterns, wherein a first stitch has a repeating pattern traversing diagonally by two or more needle positions and a second stitch has a repeating pattern alternatively traversing diagonally by three or more needle positions and then by one needle position.

44. The prosthesis of claim 41 further including a tubular layer of ePTFE circumferentially disposed and securably attached to said stent.

45. The prosthesis of claim 41 wherein said stent is a wire-stent.

46. The prosthesis of claim 41 wherein said yarns are polyethylene terephthalate polyester textured yarns having a denier of at least 30; and further wherein said polyethylene terephthalate polyester textured yarns have a denier of no more than about 100.

47. An implantable tubular prosthesis capable of longitudinal expansion from a quiescent state to an elongated state comprising:

a radially contractible and longitudinally expandable tubular stent having a quiescent diameter and quiescent length capable of longitudinal expansion to the elongated state having an elongated length and a contracted diameter, wherein the elongated length is greater than the quiescent length and the contracted diameter is smaller than the quiescent diameter, and further wherein said stent is capable of resiliently returning from the elongated state to the quiescent state; and a tubular knitted tubular graft circumferentially disposed and securably attached to said stent in the quiescent state, said graft having a pattern of yarns interlaced into stitches in a knit pattern capable of resilient longitudinal elongation and resilient radial contraction of said graft to the elongated state and having greater than about 350 stitches per square centimeter to provide compliancy in the quiescent state;

wherein said interlaced stitches of said graft form a graft wall and further wherein said graft wall has a wall thickness of at least 0.3 millimeters; and further wherein said graft wall has a wall thickness of no more than about 0.4 millimeters.

48. The prosthesis of claim 47 wherein said knit pattern is a warp knitted pattern of yarns forming a textile layer having an interior surface and an exterior surface, wherein interior yarns predominate the interior surface and form loops in the longitudinal direction of said prosthesis, and exterior yarns predominate the exterior surface and are diagonally shifted over one or more of the interior yarns in an alternating pattern along a width of said prosthesis to engage the interior yarns, and further wherein the interior yarn alternately interlaces the engaging exterior yarn to form open loops where the interior yarn does not cross over itself and closed loops where the interior yarn does cross over itself.

49. The prosthesis of claim 47 wherein said knit pattern comprising a interior and exterior yarns interlaced from single stitches, said single stitches being deposed in a plurality of stitch repeating patterns, wherein a first stitch has a repeating pattern traversing diagonally by two or more needle positions and a second stitch has a repeating pattern alternatively traversing diagonally by three or more needle positions and then by one needle position.

50. The prosthesis of claim 47 further including a tubular layer of ePTFE circumferentially disposed and securably attached to said stent.

51. The prosthesis of claim 47 wherein said stent is a wire-stent.

52. The prosthesis of claim 47 wherein said yarns are polyethylene terephthalate polyester textured yarns having a denier of at least about 30; and further wherein said polyethylene terephthalate polyester textured yarns have a denier of no more than about 80.

53. An implantable tubular graft comprising:

a tubular knitted tubular graft having a pattern of yarns interlaced into stitches in a knit pattern capable of resilient longitudinal elongation and resilient radial contraction of said graft from a quiescent state to the elongated state and having at least about 400 to 900 stitches per square centimeter and further having no more than about 900 stitches per square centimeter to provide compliancy in the quiescent state, wherein said knit pattern is a warp knitted pattern of yarns forming a textile layer having an interior surface and an exterior surface, wherein interior yarns predominate the interior surface and form loops in the longitudinal direction of said graft, and exterior yarns predominate the exterior surface and are diagonally shifted over one or more of the interior yarns in an alternating pattern along a width of said graft to engage the interior yarns, and further wherein the interior yarn alternately interlaces the engaging exterior yarn to form open loops where the interior yarn does not cross over itself and closed loops where the interior yarn does cross over itself.

54. The graft of claim 53 wherein said knit pattern comprising a interior and exterior yarns interlaced from single stitches, said single stitches being deposed in a plurality of stitch repeating patterns, wherein a first stitch has a repeating pattern traversing diagonally by two or more needle positions and a second stitch has a repeating pattern alternatively traversing diagonally by three or more needle positions and then by one needle position.

55. The graft of claim 53 wherein said yarns are polyethylene terephthalate polyester textured yarns having a denier of at least 30; and further wherein said polyethylene terephthalate polyester textured yarns having a denier of no more than 80.

* * * * *

UNITED STATES PATENT AND TRADEMARK OFFICE
CERTIFICATE OF CORRECTION

PATENT NO.    : 6,540,773 B2
DATED         : April 1, 2003
INVENTOR(S)   : Dong, Jerry Q.

It is certified that error appears in the above-identified patent and that said Letters Patent is hereby corrected as shown below:

Column 7,
Line 31, "needle position s in" should read -- needle positions in --.

Column 11,
Line 53, "the intemodal distance" should read -- the internodal distance --.

Column 18,
Line 18, "interior yam alternately" should read -- interior yarn alternately --.
Line 21, "interior yam does" should read -- interior yarn does --.

Signed and Sealed this

Eighteenth Day of November, 2003

JAMES E. ROGAN
*Director of the United States Patent and Trademark Office*